United States Patent
Baik et al.

(10) Patent No.: US 9,364,552 B2
(45) Date of Patent: Jun. 14, 2016

(54) COMPOSITION FOR INHIBITING AFTER-CATARACT AND METHOD OF PREPARING THE SAME

(75) Inventors: Yeong-Jun Baik, Seoul (KR); Choun-Ki Joo, Seoul (KR); Sung-Hee Lee, Yongin-si (KR); Jun-Sub Choi, Yongin-si (KR); Koo Woo, Gwacheon-si (KR)

(73) Assignees: BMI KOREA CO., LTD, Hwaseong-Si (KR); CATHOLIC UNIVERSITY INDUSTRY-ACADEMIC COOPERATION FOUNDATION, Seoul (KR)

( * ) Notice: Subject to any disclaimer, the term of this patent is extended or adjusted under 35 U.S.C. 154(b) by 0 days.

(21) Appl. No.: 14/364,325

(22) PCT Filed: Jan. 9, 2012

(86) PCT No.: PCT/KR2012/000205
§ 371 (c)(1),
(2), (4) Date: Jun. 11, 2014

(87) PCT Pub. No.: WO2013/089307
PCT Pub. Date: Jun. 20, 2013

(65) Prior Publication Data
US 2014/0378410 A1 Dec. 25, 2014

(30) Foreign Application Priority Data

Dec. 12, 2011 (KR) .......... 10-2011-0133103

(51) Int. Cl.
| | |
|---|---|
| *A61K 47/48* | (2006.01) |
| *A61K 31/4402* | (2006.01) |
| *A61K 9/00* | (2006.01) |
| *A61K 31/728* | (2006.01) |
| *A61K 31/655* | (2006.01) |
| *A61K 9/08* | (2006.01) |
| *A61K 9/19* | (2006.01) |

(52) U.S. Cl.
CPC ......... *A61K 47/48215* (2013.01); *A61K 9/0048* (2013.01); *A61K 9/08* (2013.01); *A61K 9/19* (2013.01); *A61K 31/4402* (2013.01); *A61K 31/655* (2013.01); *A61K 31/728* (2013.01)

(58) Field of Classification Search
CPC ... A61K 31/655; A61K 31/4402; A61K 9/19; A61K 9/08; A61K 31/728; A61K 47/48215; A61K 9/0048; A61K 2300/00
USPC .......................................................... 514/54
See application file for complete search history.

(56) References Cited

U.S. PATENT DOCUMENTS 5,093,487 A * 3/1992 Brown ................ C08B 37/0072
536/124
2014/0378410 A1 12/2014 Baik et al.

FOREIGN PATENT DOCUMENTS

| CN | 102106838 | 6/2011 |
|---|---|---|
| CN | 102225220 | 10/2011 |
| EP | 2792356 | 10/2014 |
| JP | 2008-505179 | 2/2008 |
| KR | 2003-0023098 | 3/2003 |
| KR | 2003-0069917 | 8/2003 |
| KR | 10-2008-0092631 | 10/2008 |
| KR | 10-0894042 | 10/2008 |
| KR | 20080092631 | * 10/2008 |
| WO | 2004/014399 | 2/2004 |
| WO | 2013/089307 | 6/2013 |

OTHER PUBLICATIONS

Koide Yoshihiro, et al., "P-108 Effects of various viscoelastic substances on the epithelial cell of crystalline lens", Journal of Japanese Ophthalmological Society, Mar. 15, 2010, vol. 114, p. 303.
The Search Report dated Jun. 23, 2015, Attached to the Office Action dated Jul. 1, 2015, Chinese Patent Application No. 201280069538.7.
The Examination Search Report(attached to the Office Action), Canadian Intellectual Property Office, Mar. 3, 2016, Canadian Patent Application No. 2,858,699.

* cited by examiner

*Primary Examiner* — Clinton Brooks
*Assistant Examiner* — Yih-Horng Shiao
(74) *Attorney, Agent, or Firm* — Lex IP Meister, PLLC (57) ABSTRACT

The present invention relates to a composition for inhibiting after-cataract including a hydrophilic sulfasalazine; a high content of hyaluronic acid; and a carrier containing an aqueous solution, and a method of preparing a composition for inhibiting after-cataract including the steps of adding hyaluronic acid powder to a hydrophilized sulfasalazine; and mixing the same with a specific condition.

16 Claims, 7 Drawing Sheets

A. Light Microscopy

B. Inhibitory effect

COMPOSITION FOR INHIBITING AFTER-CATARACT AND METHOD OF PREPARING THE SAME

TECHNICAL FIELD

The present invention relates to a composition for inhibiting an after-cataract and a method of preparing the same. More particularly, the invention relates to a composition for inhibiting after-cataract being capable of providing a more effective medicinal effect and a homogeneous medicine as well as lowering the disease rate of after-cataract apparently and preventing loss of eyesight due to after-cataract and a secondary operation, and a method of preparing the same.

BACKGROUND OF THE INVENTION

It is known that about 30% of total cataract surgery patients suffer from after-cataract (posterior capsular opacity), that is, a disease in which the remaining lens epithelial cells grow up and enter into the posterior capsule with an irregular array and the eye lens becomes cloudy.

Such after-cataract occurs in every age group, and particularly, it is being reported that the attack rate in the younger age groups is higher by 2 times that in the olderly.

Figure 1:
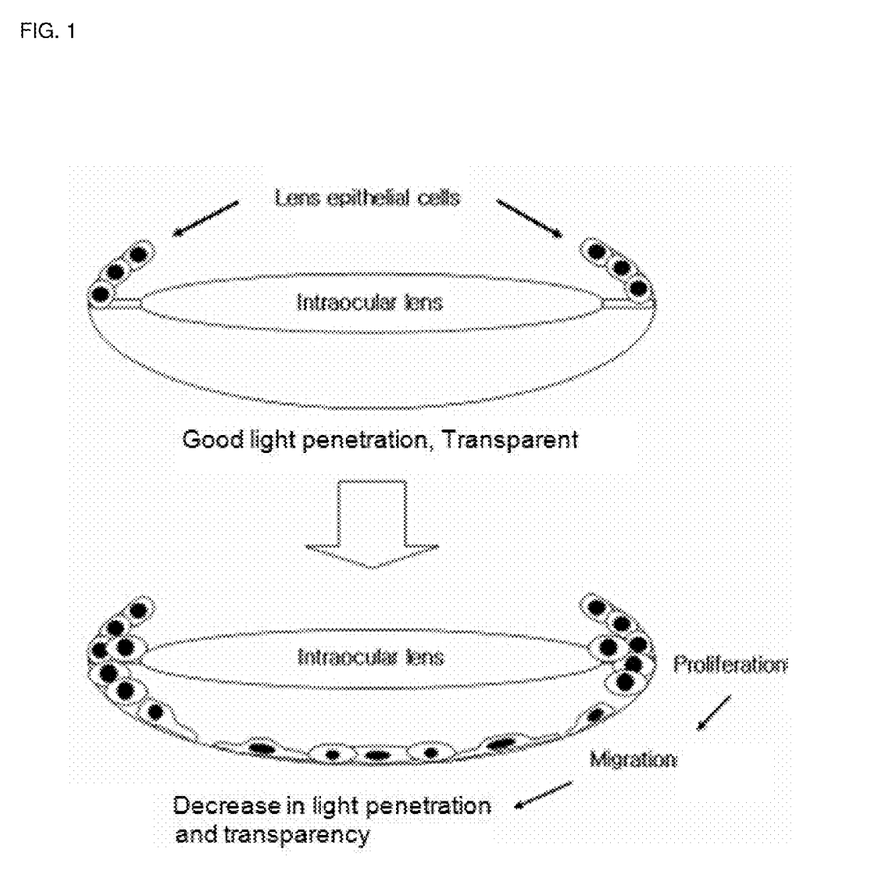
FIG. 1 shows a schematic diagram of the pathogenesis process of after-cataract.
Figure 2:
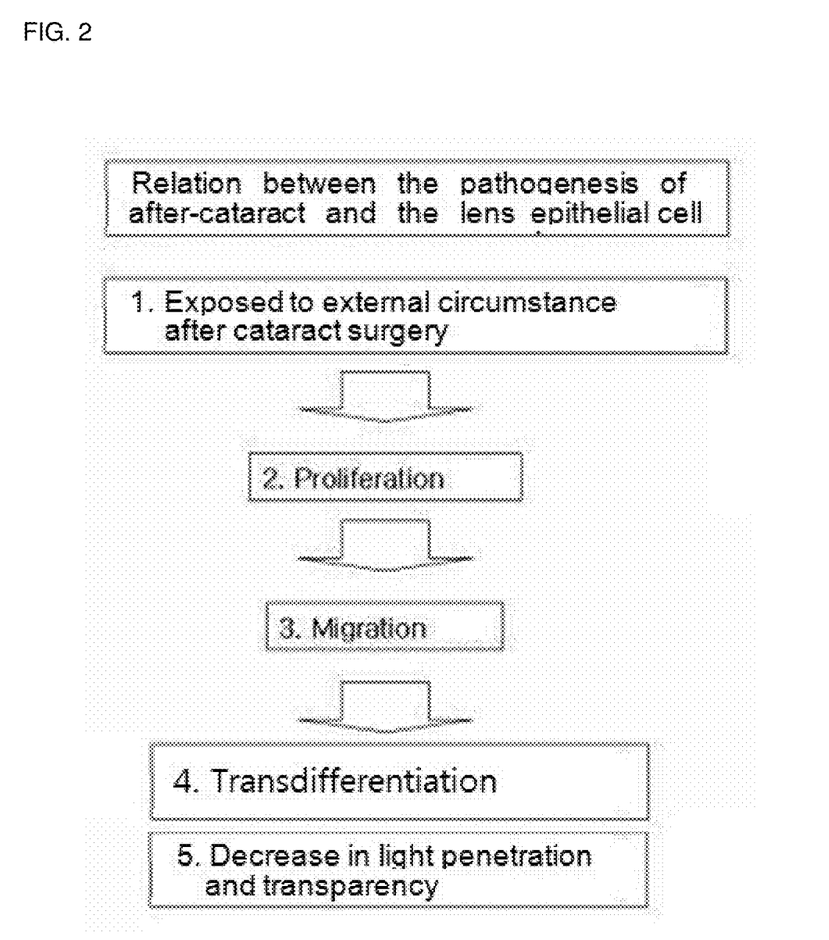
FIG. 2 shows a schematic diagram of the relationship between the pathogenesis of an after-cataract and the lens epithelial cell.

More specifically, as illustrated in FIGS. 1 and 2, the lens epithelial cells proliferate continuously proliferate when they are exposed to the external environment after the cataract operation.

Accordingly, as the lens epithelial cells migrate into the posterior lens capsule, the relatively vacant space and subsequent cell transformation and proliferation occur, the light transparency and eyesight deteriorate, and the after-cataract occurs when the lens epithelial cells gathered in the posterior capsule completely deform.

Until now, the laser (with a Nd-YAG laser) surgery has been known as the only method for treating the after-cataract, but there has been a problem that eyesight becomes narrow after the laser surgery.

Therefore, it is more effective method to treat the after-cataract preemptively, but, up to now, only a method of providing a physical change to the support for the artificial lens used in the cataract surgery and the method of using a capsular tension ring have been provided as the methods of inhibiting the after-cataract.

Korean Pat. No. 0490286 discloses an eye drops composition for treating retinal damage which can treat retinal ischemia due to glaucoma, retinal damage due to diabetic retinopathy, degeneration of the retinal nerve due to uveitis, and so on by using sulfasalazine or a water-soluble salt thereof as the active component.

Korean Pat. No. 0490286 also discloses the pharmaceutical composition which can prevent and treat cerebral nerve diseases such as Parkinson's disease, Huntington's disease, Alzheimer's disease, and the like by using sulfasalazine as the active component.

However, it has been impossible to prevent or treat the after-cataract effectively even by these methods, and there has been no known method for preventing or treating the after-cataract by inhibiting the proliferation and migration of the cataract lens epithelial cells.

DETAILS OF THE INVENTION

Objects of the Invention

The present invention relates to a composition for inhibiting after-cataract being capable of providing a more effective medicinal effect and a homogeneous medicine as well as preventing loss of eyesight due to an after-cataract and a secondary operation, and a method of preparing the same.

Means for Achieving the Objects

The present invention provides a composition for inhibiting after-cataract, including a hydrophilic sulfasalazine; 1.4 to 2.0% (w/v) of hyaluronic acid; and a carrier containing an aqueous solution.

The present invention also provides a method of preparing a composition for inhibiting after-cataract, including the steps of hydrophilizing sulfasalazine; adding hyaluronic acid powder to the hydrophilized sulfasalazine; and mixing the hydrophilized sulfasalazine and hyaluronic acid powder at 33 to 42° C. for 5 to 24 hours.

Hereinafter, the composition for inhibiting after-cataract according to specific embodiment of the invention and the preparation method thereof are explained in more detail.

According to one embodiment of the invention, a composition for inhibiting after-cataract, including a hydrophilic sulfasalazine; 1.4 to 2.0% (w/v) of hyaluronic acid; and an aqueous solution containing a carrier may be provided.

The present inventors have already revealed that it is possible to inhibit the cataract-causing proliferation and migration of the lens epithelial cells and maintain the transparency of the posterior capsule by using the sulfasalazine-hyaluronic acid mixture and a composition for inhibiting after-cataract including the same, and that it is possible to inhibit the generation of an after-cataract, in Korean Pat. No. 0894042.

However, since hyaluronic acid is a poorly soluble compound and the maximum solubility thereof is only 2% (w/v), not only does the concentration of hyaluronic acid in the composition falls short of the concentration required in the ophthalmology operation, for example, 1.4~1.5% (w/v), but also the homogeneity of the mixture is not sufficient, even if the aqueous solution including sulfasalazine and the aqueous solution including 2% (w/v) of hyaluronic acid are mixed in an identical ratio.

Therefore, the present inventors proceeded with related studies, and recognized that not only can hyaluronic acid can be included with the concentration beyond the level required in the ophthalmology operation but that the composition for inhibiting after-cataract having excellent homogeneity and after-cataract inhibition effect beyond the equivalent level can also be obtained by using the specific preparation method disclosed below, through experiments, and accomplished the present invention.

According to this, it is possible to provide such composition for inhibiting after-cataract capable of providing a medicine having more effective medicinal effect and homogeneous state of dispersion as well as lowering the disease rate of after-cataract apparently and preventing loss of eyesight due to after-cataract and a secondary operation.

Further, as shown in Experimental Examples A and C disclosed below, it is recognized that the composition for inhibiting after-cataract effectively inhibits the migration of the lens epithelial cell and can lower the disease rate of after-cataract apparently.

More specifically, it is recognized that it is possible to inhibit NF-k B from being manifested in the cell nucleus of the main active site by applying the composition for inhibiting after-cataract.

Said sulfasalazine (2-hydroxy-5-[[4-[(2-pyridinylamino) sulfonyl]azo]benzoic acid or 6-oxo-3-(2-[4-(N-pyridin-2-yl-sulfamoyl)phenyl]hydrazono)cyclohexa-1,4-dienecarboxylic acid) is a compound formed by azo-bonding of sulfapyridine and 5-aminosalicylic acid (5-ASA), and is known to inhibit the activity of NF-k B (nuclear factor kappa B).

Therefore, the composition for inhibiting after-cataract including such sulfasalazine can inhibit the pathogenesis of after-cataract by inhibiting the activity of NF-k B that is manifested when the lens epithelial cells proliferate and migrate.

Since sulfasalazine is poorly soluble in an aqueous solution, so it must be made into hydrophilic sulfasalazine by being solubilized to be used for a medicine.

Such hydrophilic sulfasalazine may be obtained in a form of an acid addition salt or an alkali addition salt by adding hydrochloric acid, sodium chloride, potassium chloride, and the like to sulfasalazine, and preferably, it may be obtained by the PEGylation of sulfasalazine.

Said hydrophilic sulfasalazine may include the PEGylated sulfasalazine.

Said PEGylated sulfasalazine may be obtained by adding sulfasalazine to a balanced salt solution including polyethylene glycol.

The balanced salt solution may include polyethylene glycols of various molecular weights with various concentrations, and it may be preferable to include a polyethylene glycol having a weight average molecular weight of 300 to 500, preferably 380 to 420, at a concentration of 1% (v/v) or more, preferably 5% (v/v) or more.

The concentration of the hydrophilic sulfasalazine may be 0.1 to 1.5 mM, preferably 0.2 to 1.2 mM, and more preferably 0.3 to 1.0 mM.

If the concentration is below 0.1 mM, it may be difficult to realize the effective medicinal effect, and if it is over 1.5 mM, the toxicity to the lens epithelial cells may be excessive when the ophthalmology operation is prolonged.

Meanwhile, since said hyaluronic acid maintains the shape of the capsule of a lens during the ophthalmology operation, it takes a role of a lubricant during the artificial lens insertion, increases the transparency and the viscosity of the composition, and makes a stable operation possible when the composition for inhibiting after-cataract is applied to an eyeball.

In the composition for inhibiting after-cataract of one embodiment of the invention, the content of hyaluronic acid may be 1.4 to 2.0% (w/v), and preferably 1.5 to 1.8% (w/v).

In the past, it has been difficult to prepare the composition including hyaluronic acid over 1.0% (w/v) and the homogeneity of the composition has been noticeably bad even though the concentration of hyaluronic acid was increased.

However, according to the specific preparation method disclosed below, the composition for inhibiting after-cataract having excellent homogeneity even while including 1.4 to 2.0% (w/v) of hyaluronic acid is provided.

If the content of the hyaluronic acid in the composition for inhibiting an after-cataract is below 1.4% (w/v), it is not preferable because it is difficult to maintain the shape of the capsule of the lens, the role of a lubricant during the artificial lens insertion may decrease, it may fail to deliver the medicinal effect of the sulfasalazine, the viscosity of the composition decreases and the time for sulfasalazine to contact with the lens epithelial cells becomes short, and thus it becomes difficult to take a play proper role as a medicine for an eyeball.

Meanwhile, hyaluronic acid having a weight average molecular weight of $1.0 \times 10^6$ to $4.0 \times 10^6$ g/mol may be used in the composition for inhibiting an after-cataract.

In the composition for inhibiting after-cataract, the relative standard deviation of the content of sulfasalazine measured by using a high performance liquid chromatography (HPLC) may be 2 or less.

According to prior arts, the phenomenon that the homogeneity remarkably decreases and the dispersion of sulfasalazine becomes very heterogeneous (for example, the phenomenon that the relative standard deviation of the content of sulfasalazine becomes very large) was observed when the content of hyaluronic acid increased in the composition including sulfasalazine and hyaluronic acid but, as shown in Experimental Example D disclosed below, it is recognized that sulfasalazine and hyaluronic acid are very homogenously dispersed in the composition for inhibiting after-cataract of one embodiment of the invention.

Accordingly, the composition for inhibiting an after-cataract can resolve the problems that sulfasalazine contacts to a particular part with an excessive concentration and shows toxicity to the lens epithelial cell or contacts with a low concentration and the effective medicinal effect is not manifested, and it can provide a very stable medicine for an ophthalmology operation because sulfasalazine can uniformly contact to the whole area of the lens epithelial cell when the composition for inhibiting after-cataract is applied to an ophthalmology operation.

Furthermore, it is possible to minimize the inconvenience of the secondary medication in surgery and the burden of risk to the additional toxicity because sulfasalazine and hyaluronic acid are used together when the composition for inhibiting after-cataract is applied to an ophthalmology operation.

Meanwhile, the carrier containing an aqueous solution may include distilled water, a phosphate buffered saline, a balanced salt solution, a saline solution, or a mixture thereof.

The composition for inhibiting after-cataract may further include a pharmaceutically acceptable salt.

For example, the pharmaceutically acceptable salt may be hydrochloric acid, sodium chloride, potassium chloride, or a mixture thereof.

Meanwhile, according to another embodiment of the invention, a method of preparing a composition for inhibiting after-cataract, including the steps of hydrophilizing sulfasalazine; adding hyaluronic acid powder to the hydrophilized sulfasalazine; and mixing the hydrophilized sulfasalazine and hyaluronic acid powder at 33 to 42° C. for 5 to 24 hours may be provided.

The present inventors proceeded the studies about the composition for inhibiting after-cataract, and recognized that it is possible to increase not only the concentration of hyaluronic acid but also the homogeneity of the composition and to provide the composition for inhibiting after-cataract having excellent medicinal effect and stability, by adding hyaluronic acid powder to the hydrophilized sulfasalazine and mixing the same in a specific reaction condition, through experiments, and accomplished the present invention.

It is preferable that the hydrophilized sulfasalazine and the hyaluronic acid powder are mixed at the temperature of 33 to 42° C., preferably of 35 to 40° C., for 5 to 24 hours, preferably for 10 to 15 hours.

When the mixing temperature is below 33° C., the components of the composition for inhibiting after-cataract may not be mixed uniformly, and when it is over 42° C., it is not preferable because it is not easy to prepare the medicine stably.

Further, when the mixing time is below 5 hours, the components of the composition for inhibiting after-cataract may not be mixed uniformly, and when it is over 24 hours, a change may take place in the viscosity of the hyaluronic acid.

As shown in Experimental Example D disclosed below, it is recognized that the compositions for inhibiting after-cataract prepared by mixing the hydrophilized sulfasalazine and the hyaluronic acid powder at a temperature of 35° C. (Example 4), 37° C. (Example 1), and 40° C. (Example 3) show a relative standard deviation of the content of sulfasalazine of 2 or less, and the components of the composition for inhibiting after-cataract are very homogeneously dispersed.

On the contrary, when the mixing temperature is 25° C. (Comparative Example 1), it is recognized that it shows a high relative standard deviation of 20% or more and the components of the composition for inhibiting after-cataract are very heterogeneously dispersed.

In the hydrophilizing step of sulfasalazine, any known method for solubilizing a poorly soluble compound may be used unlimitedly, but preferably, the step of PEGylation of sulfasalazine may be applied to the method.

Particularly, the step of PEGylation step of sulfasalazine may include the step of adding sulfasalazine to a balanced salt solution including polyethylene glycol.

The polyethylene glycol included in the balanced salt solution can hydrophilize sulfasalazine through the PEGylation.

When sulfasalazine is hydrophilized through the PEGylation, it can be used as a water-soluble liquid without changing the chemical structure and can be easily prepared into injections and an ophthalmic medicine.

Specific features of sulfasalazine and polyethylene glycol are as disclosed above.

The step of hydrophilizing sulfasalazine may include the step of regulating the concentration of sulfasalazine to be 0.1 to 1.5 mM.

More specifically, the concentration of sulfasalazine may be regulated to 0.1 to 1.5 mM, preferably 0.2 to 1.2 mM, and more preferably 0.3 to 1.0 mM by adding a proper amount of sulfasalazine solution to the balanced salt solution including polyethylene glycol.

The step of adding hyaluronic acid powder to the hydrophilized sulfasalazine may include the step of regulating the concentration of hyaluronic acid to be 1.4 to 2.0% (w/v), and preferably 1.5 to 1.8% (w/v).

More specifically, the concentration may be regulated by adding a proper amount of hyaluronic acid powder to the balanced salt solution in which said hydrophilized sulfasalazine or sulfasalazine is included.

There are no limitations on the properties, shape, size, and the like of the hyaluronic acid powder and an axenic one may be preferably used.

Meanwhile, the preparation method of the composition for inhibiting after-cataract may further include the step of adding a pharmaceutically acceptable additive, carrier, or salt.

Such pharmaceutically acceptable carrier or salt may be added in the process of preparing the composition for inhibiting after-cataract without limitation but it is preferable to add the same after the hydrophilized sulfasalazine and the hyaluronic acid powder are completely mixed.

Effects of the Invention

According to the present invention, it is possible to provide a composition for inhibiting after-cataract capable of providing more effective medicinal effect and a stable medicine, as well as lowering the disease rate of after-cataract apparently and preventing loss of eyesight due to after-cataract and a secondary operation.

DETAILED DESCRIPTION OF THE EMBODIMENT

The present invention is explained in more detail by referring to the following examples.

However, the following examples are only for illustrating the present invention and the details of the present invention are not limited to or by them.

EXAMPLES AND COMPARATIVE EXAMPLES

Preparation of the Composition for Inhibiting After-Cataract

Example 1

Sulfasalazine was added to 500 mL of a balanced salt solution including 10% (v/v) of polyethylene glycol (PEG, Mw.400, product name: P3265, Sigma Co.) to have a concentration of 0.5 mM, and the solution was mixed for 2 hours at room temperature.

Further, hyaluronic acid powder (sodium hyaluronate, NOVA Biotech) was added in the amount of 15 g/L to the balanced salt solution including sulfasalazine and mixed for 12 hours at 37° C., and then the composition for inhibiting after-cataract, the mixture of sulfasalazine and hyaluronic acid, was obtained.

Example 2

The composition for inhibiting after-cataract was obtained substantially according to the same method as in Example 1, except that the concentration of sulfasalazine was 1.0 mM.

Example 3

The composition for inhibiting after-cataract was obtained substantially according to the same method as in Example 1, except that the mixing temperature of the balanced salt solution including sulfasalazine and the hyaluronic acid powder was 40° C.

Example 4

The composition for inhibiting after-cataract was obtained substantially according to the same method as Example 1, except that the mixing temperature of the balanced salt solution including sulfasalazine and the hyaluronic acid powder was 35° C.

Example 5

The composition for inhibiting after-cataract was obtained substantially according to the same method as in Example 1, except that the concentration of sulfasalazine was 0.3 mM.

Comparative Example 1

The composition for inhibiting after-cataract was obtained substantially according to the same method as Example 1, except that the mixing temperature of the balanced salt solution including sulfasalazine and the hyaluronic acid powder was 25° C.

Comparative Example 2

Sulfasalazine was added to 500 mL of a balanced salt solution including 10% (v/v) of polyethylene glycol (PEG, Mw.400, product name: P3265, Sigma Co.) to have a concentration of 1.0 mM, and the solution was mixed for 1 hours at room temperature.

2% of hyaluronic acid solution was added to the balanced salt solution including sulfasalazine in the weight ratio of 50:50 and mixed for 2 hours at 25° C., and then the composition for inhibiting after-cataract, the mixture of sulfasalazine and hyaluronic acid, was obtained.

Comparative Example 3

The composition for inhibiting after-cataract was obtained substantially according to the same method as in Comparative Example 2, except that the concentration of sulfasalazine was 0.5 mM.

The concentration of sulfasalazine, the amount (concentration) of hyaluronic acid, and the mixing temperature of the balanced salt solution including sulfasalazine and the hyaluronic acid powder in Examples 1 to 5 and Comparative Examples 1 to 3 are listed in the following Table 1.

TABLE 1

| | Concentration of Sulfasalazine (mM) | Hyaluronic acid (amount, concentration) | Mixing temperature of Balanced salt solution including sulfasalazine and Hyaluronic acid powder (° C.) |
|---|---|---|---|
| Example 1 | 0.5 | 15 g/L, 1.5% (w/v) | 37 |
| Example 2 | 1.0 | 15 g/L, 1.5% (w/v) | 37 |
| Example 3 | 0.5 | 15 g/L, 1.5% (w/v) | 40 |
| Example 4 | 0.5 | 15 g/L, 1.5% (w/v) | 35 |
| Example 5 | 0.3 | 15 g/L, 1.5% (w/v) | 37 |
| Comparative Example 1 | 0.5 | 15 g/L, not measurable | 25 |
| Comparative Example 2 | 1.0 | 1:1 mixture of solutions, 1.0% (w/v) | 25 |
| Comparative Example 3 | 0.5 | 1:1 mixture of solutions, 1.0% (w/v) | 25 |

* In the case of Comparative Example 1, as disclosed below, the mixture of sulfasalazine and hyaluronic acid was formed very heterogeneously and it was impossible to measure exact concentration of hyaluronic acid because a respectable amount of hyaluronic acid was not dissolved therein.

EXPERIMENTAL EXAMPLES

Preparation Example 1

Human Lens Epithelial Cell Culture

A human lens epithelial B3 cell line (hereinafter, "HLE B3 cells") was added to a culture medium including 20% fetal bovine serum and Eagle's minimum essential medium (MEM, Invitrogen-Gibco, Grand Island, N.Y., USA), and the cells were cultured at 37° C. by using a 5% $CO_2$ cell incubator.

Preparation Example 2

Lens Capsule Culture

A pig eye was used. After separating the lens and cutting the front of the lens capsule into about a 5 mm diameter, a capsular tension ring (CTR98-A, Lucid Korea, Korea) was inserted in the capsule and the contents of the lens were eliminated.

Such lens capsule was put in the serumless Dulbeccos Modified essential medium (DMEM) culture solution and cultured at 37° C. by using a 5% $CO_2$ cell incubator.

After mixing the compositions for inhibiting after-cataract prepared in the Examples and Comparative Examples and the human lens epithelial cell culture solution obtained in Preparation Example 1 in the same ratio of 1:1, the mixture was put in the lens capsule of Preparation Example 2 and the effect was observed.

The methods for analyzing the effect are as follows.
1) Cell toxicity: analyzed by using a MTT assay.
2) Protein activity: carried out by using a Western blot analysis method.

Statistical analysis of all the results obtained was carried out by using one-way ANOVA test.

A. Identification of the Migration Inhibition of the Lens Epithelial Cell

The compositions for inhibiting after-cataract of Examples 1 and 2 and the control group that was not treated with sulfasalazine were mixed with the human lens epithelial cell culture solution obtained in Preparation Example 1 in the same ratio of 1:1 respectively, and the mixtures were put in the lens capsule of Preparation Example 2. After that, whether the migration of the lens epithelial cell was inhibited was observed by using a microscope (AE-21, Pelco Co.) and a photomicroscope (Digital 352 CCD, Motic Co.) and the results are listed in FIG. 3.

Figure 3:
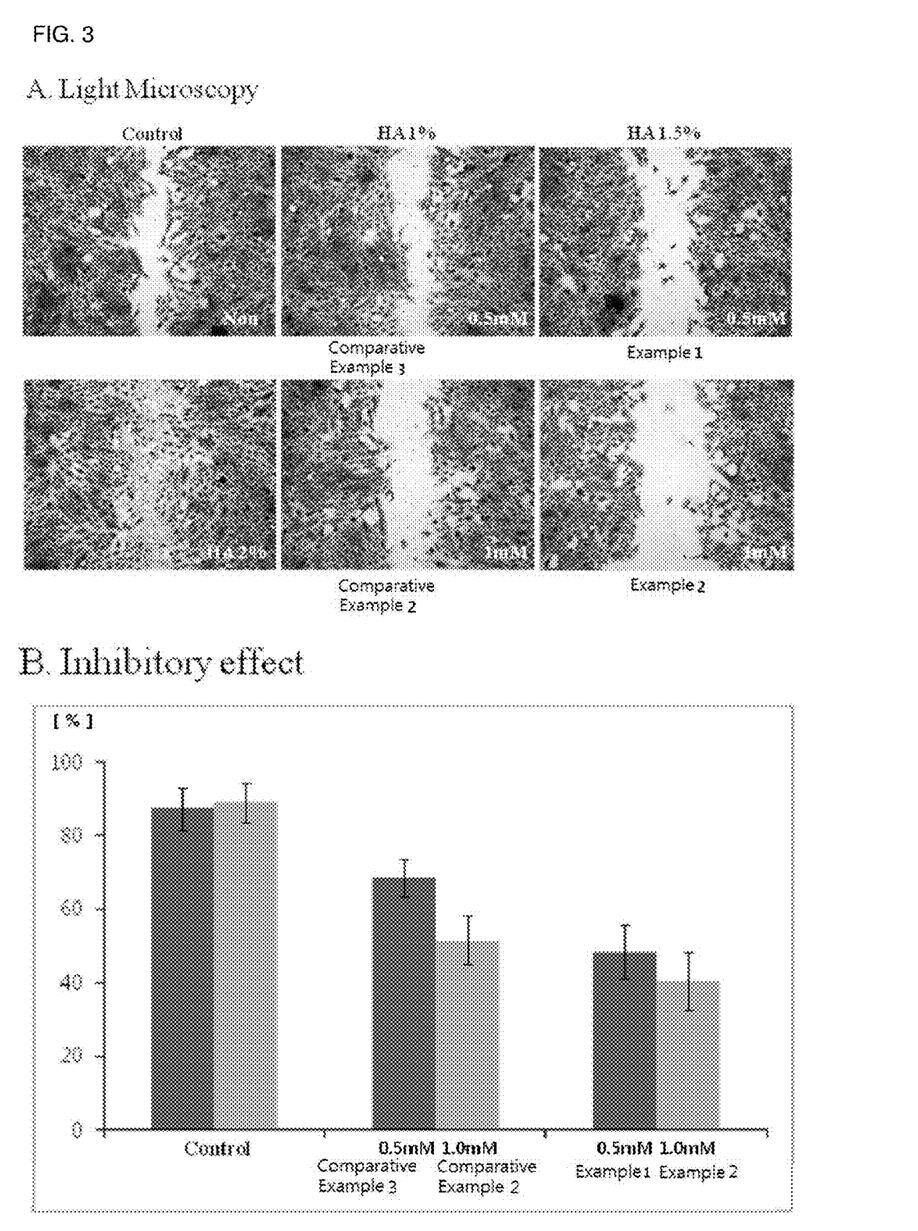
FIG. 3 shows the result of determining whether the composition for inhibiting after-cataract according to examples inhibited the migration of the lens epithelial cell or not and the statistical data regarding the same.

As shown in FIG. 3-A, it is recognized that the migration of the lens epithelial cell was inhibited by the compositions for inhibiting after-cataract of Examples 1 and 2, compared to the control group that was not treated with sulfasalazine, It is also recognized that the compositions for inhibiting after-cataract of Examples 1 and 2 can inhibit the migration of the lens epithelial cell more effectively than the compositions of Comparative Examples 2 and 3 (in which 2% of hyaluronic acid solution was mixed with the balanced salt solution including sulfasalazine in the weight ratio of 50:50).

Specifically, as shown in FIG. 3-B, the compositions for inhibiting after-cataract of Examples 1 and 2 show the migration inhibition of the lens epithelial cell and the proliferation inhibition effects of 51.5% and 40.5%, respectively. On the contrary, the compositions of Comparative Examples 2 and 3 show the migration inhibition of the lens epithelial cell and the proliferation inhibition effects of just 68.5% and 48.5%, respectively.

Figure 4:
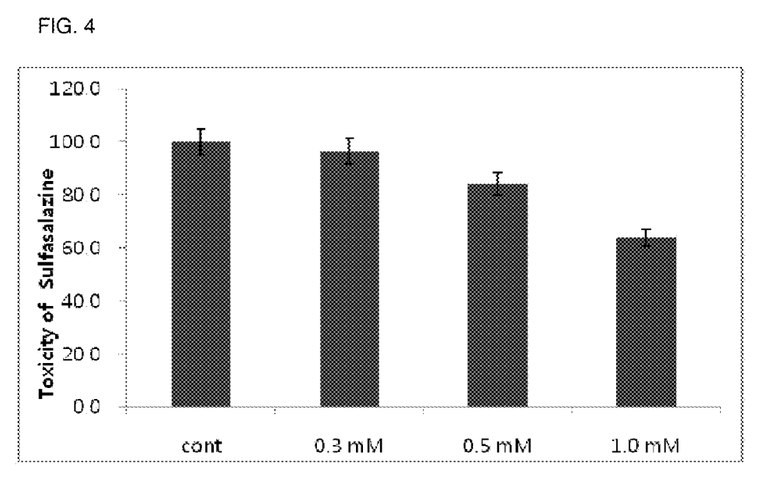
FIG. 4 shows the result of the toxicity to the cells by concentrations identified through MTT assay.

B. Experiment for Identifying the Cell Toxicity by Concentrations of Sulfasalazine As shown in FIG. 4, it is recognized that the compositions of Examples 1, 2, and 5 show the values of 60.0% or more and that was no attentive cell toxicity from the result of the MTT assay.

C. Experiment for Identifying the Manifestation and Activation Inhibition of NF-k B Whether the compositions for inhibiting after-cataract of the Examples inhibited the manifestation and the activation of NF-k B or not during the migration of the lens epithelial cells was identified by the following method.

Figure 5:
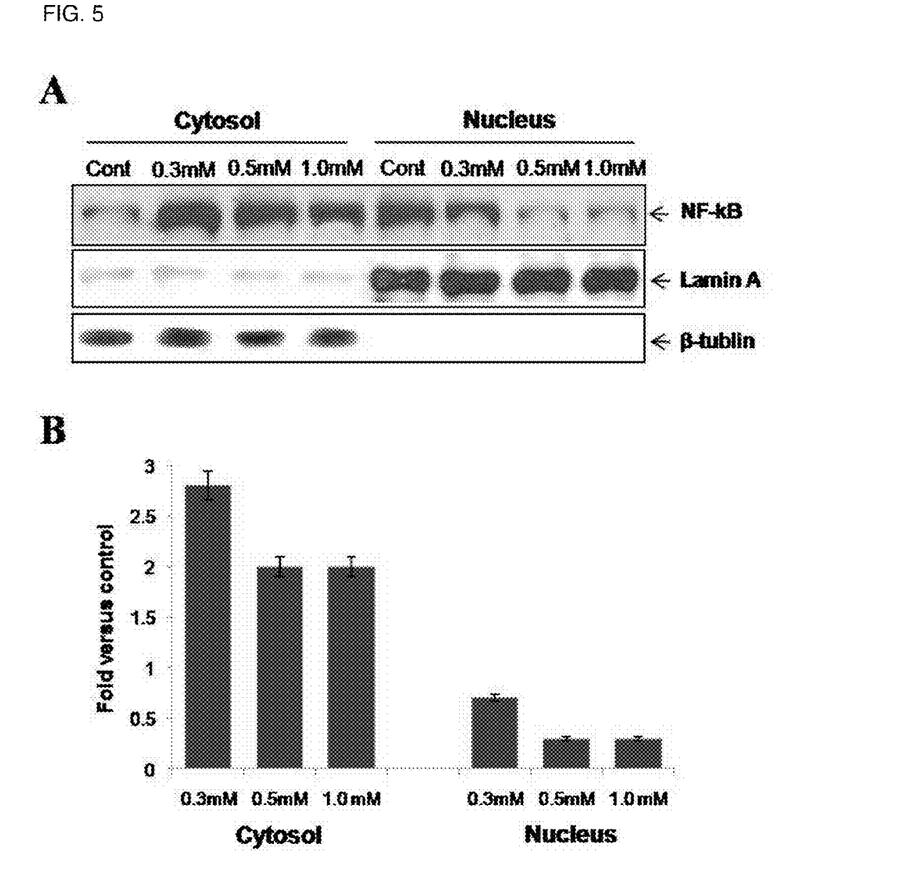
FIG. 5 shows whether NF-kB is activated in the cytoplasm and the nucleus and the statistical data regarding the same.

At first, whether NF-k B was activated in the cytoplasm and the nucleus was checked through an electro-phoresis test, and the result is shown in FIG. 5-A.

At this time, Beta-tubulin was used as a cytoplasm marker and Laminin A as a nucleus protein marker.

As shown in FIG. 5A, it is recognized that NF-k B is manifested in the cytoplasm and that the nucleus during the migration of the lens epithelial cell and the main active site is the nucleus of the cell (control group).

On the contrary, it is recognized that the manifestation of NF-k B in the nucleus of the cell, the main active site, was inhibited when the compositions for inhibiting after-cataract of Examples 1, 2, and 5 were applied.

Further, as shown in FIG. 5-B, it is shown that the migration of NF-k B to the nucleus was inhibited by 30% or more when the compositions for inhibiting after-cataract of the Examples were applied.

D. Evaluation on the Homogeneity of the Sulfasalazine-Hyaluronic Acid Mixture (1) Sulfasalazine was dissolved in the balanced salt solution including 10% polyethylene glycol by concentrations, and the concentration of sulfasalazine was measured by a high performance liquid chromatography (HPLC) and the linear calibration line was obtained (FIG. 6-A).

(2) Three samples were taken from upper, middle, and lower parts of the compositions of Example 1 (37° C.), Example 3 (40° C.), Example 4 (35° C.), and Comparative Example 1 (25° C.), and the concentration of sulfasalazine was measured by using a high performance liquid chromatography (HPLC).

And, such concentration analysis was repeated 3 times and the relative standard deviation (RDS) of the concentration was calculated therefrom.

Figure 6:
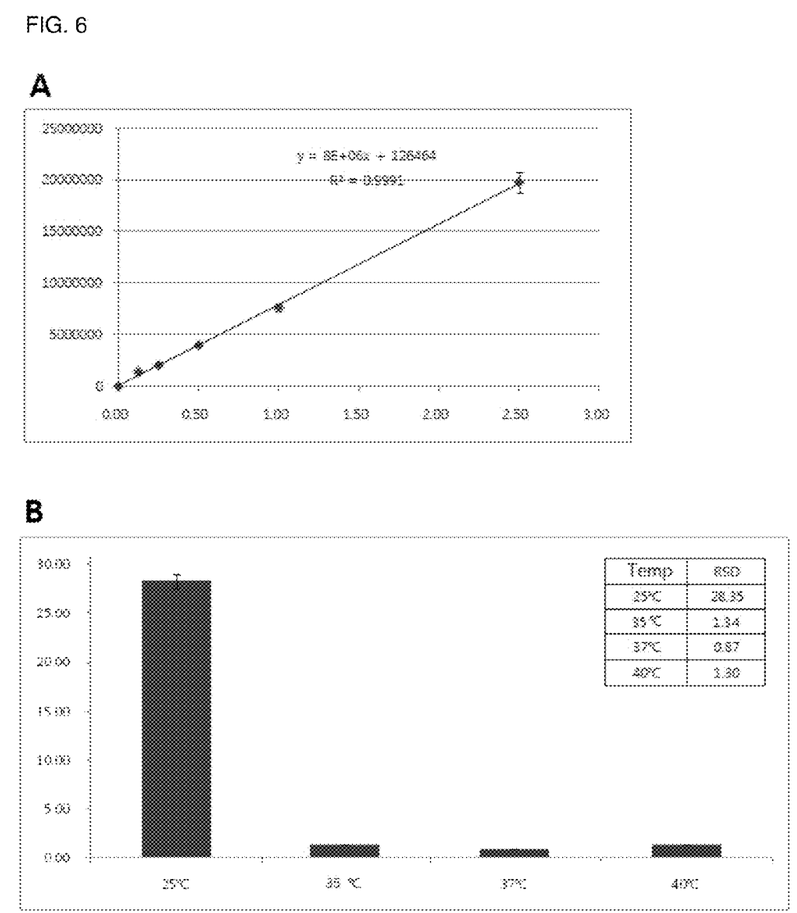
FIG. 6 shows the homogeneity evaluation result of the compositions for inhibiting after-cataract of Examples 1, 3, and 4 and Comparative Example 1.

As shown in FIG. 6B, it is recognized that Example 1 (37° C.), Example 3 (40° C.), and Example 4 (35° C.) showed the relative standard deviations of 0.87%, 1.30%, and 1.34%, respectively, and that the compositions for inhibiting after-cataract were very homogeneously dispersed.

On the contrary, it is recognized that Comparative Example 1 (25° C.) showed a high relative standard deviation of 28.35% and that the composition for inhibiting after-cataract was very heterogeneously dispersed.

Furthermore, it is recognized in the composition of Comparative Example 1 that it is impossible to obtain the composition including hyaluronic acid in a high concentration of 1.4% (w/v) or more because not only were hyaluronic acid and sulfasalazine were very heterogeneously dispersed but also a confimable amount of hyaluronic acid was not dissolved.

Figure 7:
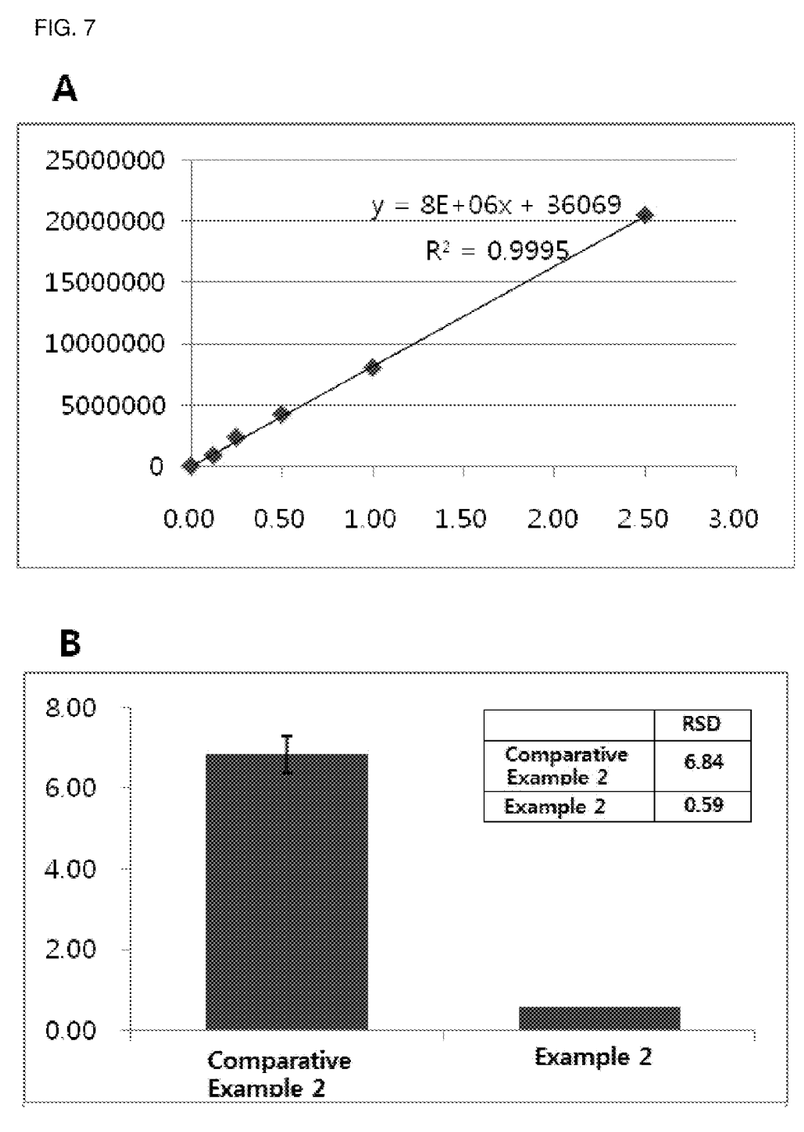
FIG. 7 shows the homogeneity evaluation result of the compositions for inhibiting after-cataract of Example 2 and Comparative Example 2.

(3) Sulfasalazine was dissolved in the balanced salt solution including 10% polyethylene glycol by concentrations, and the concentration of sulfasalazine was measured by a high performance liquid chromatography (HPLC) and a linear calibration line was obtained (FIG. 7A).

Three samples were taken from upper, middle, and lower parts of the compositions of Example 2 and Comparative Example 2, and the concentration of sulfasalazine was measured by using a high performance liquid chromatography (HPLC).

And, such concentration analysis was repeated 3 times and the relative standard deviation (RDS) of the concentration was calculated therefrom.

As shown in FIG. 7B, it is recognized that Example 2 showed a relative standard deviation of 0.59% and the composition for inhibiting after-cataract was very homogeneously dispersed but Comparative Example 2 showed the relative standard deviations of 6.84% and the composition was very heterogeneously dispersed.

The invention claimed is:

1. A composition for inhibiting after-cataract, comprising:
   a hydrophilic sulfasalazine;
   1.4 to 2.0% (w/v) of hyaluronic acid; and
   a carrier containing an aqueous solution,
   wherein the relative standard deviation of a content of sulfasalazine in the composition is 2 or less, and the hydrophilic sulfasalazine and the hyaluronic acid are prepared by mixing the hydrophilized sulfasalazine and hyaluronic acid powder at 33 to 42° C. for 5 to 24 hours.

2. The composition for inhibiting after-cataract according to claim 1, wherein the hydrophilic sulfasalazine includes a PEGylated sulfasalazine.

3. The composition for inhibiting after-cataract according to claim 1, wherein a concentration of the hydrophilic sulfasalazine is 0.1 to 1.5 mM.

4. The composition for inhibiting after-cataract according to claim 1, wherein the carrier containing an aqueous solution comprises one or more pharmaceutically acceptable carriers selected from the group consisting of distilled water, phosphate buffered saline, a balanced salt solution, and a saline solution.

5. The composition for inhibiting after-cataract according to claim 1, further comprising one or more pharmaceutically acceptable salts selected from the group consisting of hydrochloric acid, sodium chloride, and potassium chloride.

6. The composition according to claim 1, wherein the composition is used as medicine for ocular administration.

7. A method of preparing a composition for inhibiting after-cataract, comprising the steps of:
   hydrophilizing sulfasalazine;
   adding hyaluronic acid powder to the hydrophilized sulfasalazine; and
   mixing the hydrophilized sulfasalazine and hyaluronic acid powder at 33 to 42° C. for 5 to 24 hours, wherein the step of adding hyaluronic acid powder to the hydrophilized sulfasalazine comprises the step of regulating a concentration of the hyaluronic acid to be 1.4 to 2.0% (w/v).

8. The method of preparing a composition for inhibiting after-cataract according to claim 7, wherein the step of hydrophilizing the sulfasalazine comprises the step of PEGylating the sulfasalazine.

9. The method of preparing a composition for inhibiting after-cataract according to claim 8, wherein the step of PEGylating the sulfasalazine comprises the step of adding sulfasalazine to a balanced salt solution including polyethylene glycol.

10. The method of preparing a composition for inhibiting after-cataract according to claim 7, wherein the step of hydrophilizing the sulfasalazine comprises the step of regulating a concentration of sulfasalazine to be 0.1 to 1.5 mM.

11. A method of inhibiting after-cataract, comprising administering a composition of any one of claims 1 to 6, to a subject in need thereof.

12. The method of inhibiting after-cataract according to claim 11, wherein the composition is any one of claims 1 and 3 to 6, and the hydrophilic sulfasalazine includes a PEGylated sulfasalazine.

13. The method of inhibiting after-cataract according to claim 11, wherein the composition is any one of claims 1, 2, and 4 to 6, and a concentration of the hydrophilic sulfasalazine is 0.1 to 1.5 mM.

14. The method of inhibiting after-cataract according to claim 11, wherein composition is any one of claims 1 to 3, 5, and 6, and the carrier containing an aqueous solution comprises one or more pharmaceutically acceptable carriers selected from the group consisting of distilled water, phosphate buffered saline, a balanced salt solution, and a saline solution.

15. The method of inhibiting after-cataract according to claim 11, wherein the composition is any one of claims 1 to 4 and 6, and the composition further comprises one or more pharmaceutically acceptable salts selected from the group consisting of hydrochloric acid, sodium chloride, and potassium chloride.

16. The method of inhibiting after-cataract according to claim 11, wherein the composition is any one of claims 1 to 5, and the composition is used for ocular administration.

* * * * *